US00PP34289P2

(12) United States Plant Patent
Lim

(10) Patent No.: US PP34,289 P2
(45) Date of Patent: Jun. 7, 2022

(54) FLORIBUNDA ROSE PLANT NAMED 'ALTSISTER'

(50) Latin Name: *Rosa hybrida*
Varietal Denomination: ALTsister

(71) Applicant: Altman Specialty Plants, Inc, Vista, CA (US)

(72) Inventor: Peter Lim, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/356,891

(22) Filed: Jun. 24, 2021

(51) Int. Cl.
*A01H 5/02* (2018.01)
*A01H 6/74* (2018.01)

(52) U.S. Cl.
USPC ..... Plt./143

(58) Field of Classification Search
USPC ..... Plt./141–143, 130–132, 102
CPC ..... A01H 5/02; A01H 5/00; A01H 5/0222; A01H 5/08; A01H 6/74; A01H 6/749
See application file for complete search history.

(56) References Cited

PUBLICATIONS

Altman Plants True Bloom Roses 2018, retrieved on Sep. 1, 2021, retrieved from the Internet at https://altmanplants.com/introducing-true-bloom-roses/, 3 pp. (Year: 2018).*

Grief, Rose Varieties: What are some different types of roses, retrieved on Sep. 14, 2021, retrieved from the Internet at https://www.gardeningknowhow.com/ornamental/flowers/roses/different-types-of-roses.htm, 2021, 5 pp. (Year: 2021).*

* cited by examiner

*Primary Examiner* — June Hwu
(74) *Attorney, Agent, or Firm* — Cassandra Bright

(57) ABSTRACT

A new and distinct hybrid floribunda *Rosa* plant having cultivar name 'ALTsister' is disclosed, characterized by double flowers uniquely colored pink-orange and yellow. Plants are vigorous and can be grown on their own roots. Foliage is glossy and exhibits good resistance to blackspot and powdery mildew diseases. Flowering begins early and plants exhibit strong continuous blooming. The new variety is a *Rosa*, normally produced as an outdoor garden or container plant.

2 Drawing Sheets

Latin name of the genus and species: *Rosa hybrida.*
Variety denomination: 'ALTsister'.

BACKGROUND OF THE INVENTION

The new *Rosa* cultivar is a product of a planned breeding program conducted by the inventor, Peter Lim. The objective of the breeding program was to produce vigorous new garden hybrid tea rose varieties for ornamental commercial applications. The cross resulting in this new variety was made during May of 2014.

The seed parent is an unpatented, unnamed variety pure yellow floribunda type rose. The pollen parent is the variety *Rosa* 'Baiprez', U.S. Plant Pat. No. 16,408. The new variety was first selected in June 2015 by the inventor in a group of seedlings resulting from the 2014 crossing, in a nursery in Vista, Calif.

Asexual reproduction of the new cultivar has been performed by vegetative cuttings. This was first performed at a commercial nursery in in Vista, Calif. in June 2015 and has shown that the unique features of this cultivar are stable and reproduced true to type in successive generations.

SUMMARY OF THE INVENTION

The cultivar 'ALTsister' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsister' These characteristics in combination distinguish 'ALTsister' as a new and distinct *Rosa* cultivar:

1. Vigorous plant which can be grown on its own roots.
2. Double flowers colored pink-orange and yellow.
3. Glossy foliage with strong resistance to black spot disease and powdery mildew.
4. Strong continuous blooming on vigorous plants.
5. Early blooming.

Plants of the new cultivar 'ALTsister' are similar to plants of the seed parent, in most horticultural characteristics, however, plants of the new cultivar 'ALTsister' differ in the following:

1. The new variety has a multi-color flower; the seed parent has a solid yellow flower.

Plants of the new cultivar 'ALTsister' are similar to plants of the pollen parent in most horticultural characteristics, however, plants of the new cultivar 'ALTsister' differ in the following;

1. The new variety produces flowers with more petals than the pollen parent.
2. Plants of the new variety are more vigorous, but shorter than plants of the pollen parent.

3. Plants of the new variety are less prone to black spot disease.

COMMERCIAL COMPARISON

Plants of the new cultivar 'ALTsister' can be compared to the commercial variety *Rosa*, 'Wekplapic', U.S. Plant Pat. No. 11,517. These varieties are similar in most horticultural characteristics, however 'ALTsister' differs in the following:

1. 'ALTsister' produces flowers with more petals.
2. 'Wekplapic' produces-petals with much more white coloration in the center.
3. The new variety is fragrant, this comparator is not fragrant.

BRIEF DESCRIPTION OF THE PHOTOGRAPHS

Figure 1:
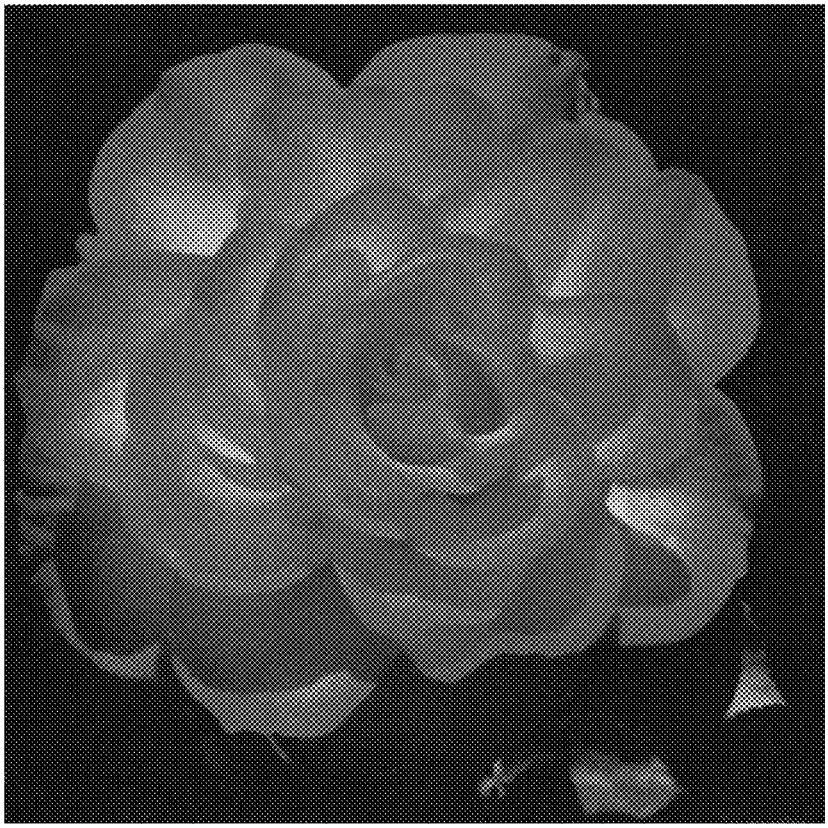

The accompanying photograph in FIG. 1 illustrates in full color a close up of an individual flower.

Figure 2:
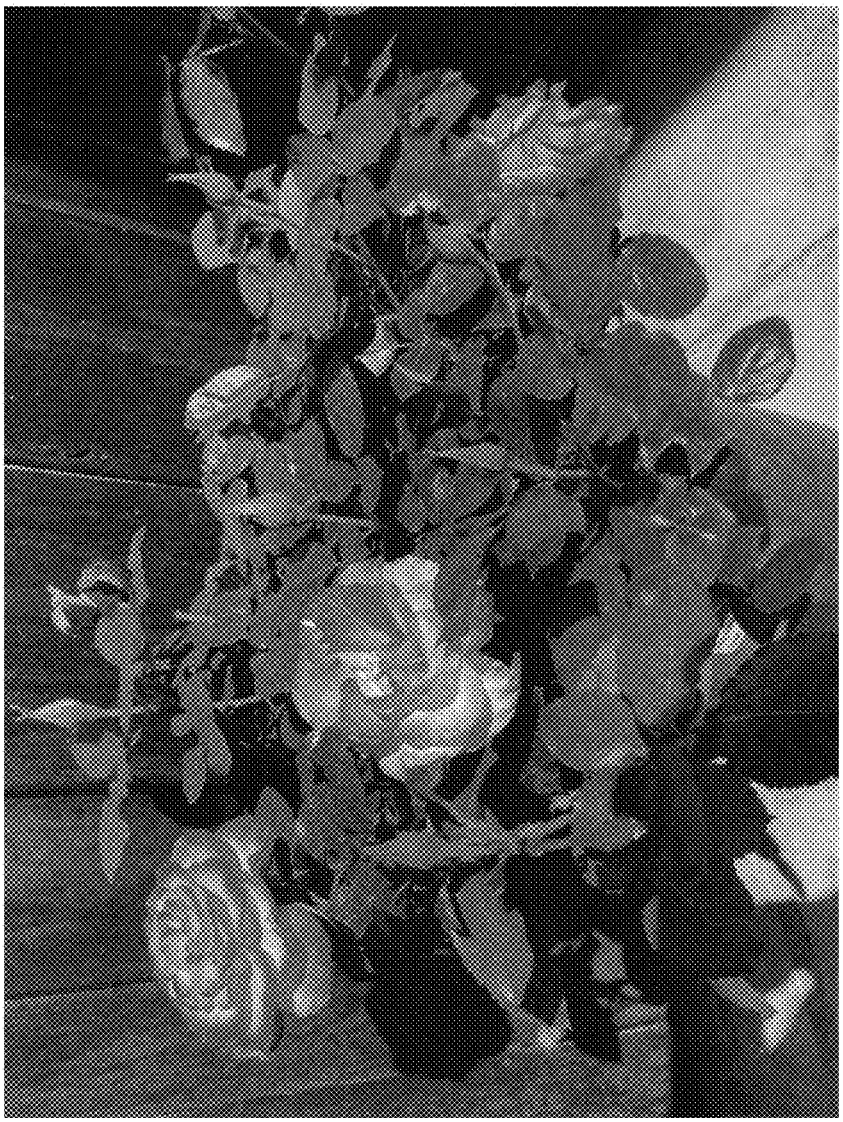

FIG. 2 illustrates a plant of approximately 18 months in a 2 gallon container during May, in Southern California.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ALTsister' plants grown outdoors, in Vista, Calif. The growing temperature ranged from approximately 10° C. to 38° C. during the day and from approximately 5° C. to 22° C. during the night. Measurements were taken in May 2021. General light conditions were very bright, normal sunlight. Measurements and numerical values represent averages of typical plant types.

Botanical classification: *Rosa* 'ALT sister'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 2 years.

Growth habit: Compact, dense, semi-upright.

Container size: 2 gallon.

Height: 38 cm.

Plant spread: 40 cm.

Rootstock: Own root.

Growth rate: Moderate.

Branching characteristics: Sympodial branching.

Length of primary lateral branches: Average range 8 to 12 cm.

Diameter of lateral branches: Approximately 4 to 6 mm.

Quantity branches: 6 to 8 main branches, moderate lateral branches, 10 to 20 lateral branches per main branch.

Branches—young wood:

*Diameter*.—Approximately 4 mm.

*Texture*.—Glabrous, dense soft, short thorns.

*Approximately density/quantity of prickles*.—Dense.

*Color*.—Near Yellow-Green 144A, flushed Greyed-Red 183B.

Branches—old wood:

*Diameter*.—Approximately 5 to 9 mm.

*Color*.—Near Green 137A.

*Texture*.—Glabrous.

*Thorns*.—Approximately density/quantity of thorns: Dense. Approximately 3 per linear cm. Color of thorns: Immature: Near Green 138B, apex Greyed-Orange 174A. Mature: Near Greyed-Orange 177C, flushed Greyed-Orange 176B. Shape: Narrow deltoid, weakly to moderately hooked. Height: Average 12 mm. Diameter: Base near 6 mm. Tip near 2 mm.

Young shoot anthocyanin: Weak to medium. Slight to moderate flush of Greyed-Red 178B or 178C.

FOLIAGE

Leaf:

*Arrangement*.—Alternate and compound.

*Quantity*.—Average 8 to 12 per main branch.

*Internode*.—Average range 2 to 3.5 cm.

*Average length*.—Approximately 12 to 15 cm.

*Average width*.—Approximately 9 to 12 cm.

Rachis:

*Average length*.—Approximately 5.5 cm.

*Average diameter*.—Approximately 0.3 cm.

*Color*.—Near Green 137C.

*Texture*.—Glabrous all surfaces. Spined along margin.

Leaflet:

*Quantity*.—3 or 5 per leaf, most commonly 5.

*Average length*.—Approximately 6 to 7 cm.

*Average width*.—Approximately 4 to 5 cm.

*Shape of blade*.—Ovate.

*Apex*.—Acute.

*Base*.—Rounded.

*Margin*.—Serrate.

*Appearance of top surface*.—Very glossy.

*Appearance of bottom surface*.—Matte.

*Texture of top surface*.—Glabrous.

*Texture of bottom surface*.—Glabrous.

*Color*.—Young foliage upper side: Near Green 137A, completely covered in dark flush Greyed-Purple 187A and 187B. Young foliage under side: Near Greyed-Purple 183A. Mature foliage upper side: Near Green 139A. Mature foliage under side: Near Green 137C.

*Venation*.—Type: Reticulate. Venation color upper side: Near Green 137A. Venation color under side: Near Green 138B.

Petiole:

*Average length*.—Approximately 4 cm.

*Average diameter*.—Approximately 3 mm.

*Color*.—Upper surface: Near Green 137B. Lower surface: Near Green 137C.

*Petiole wing*.—Typically 20 mm long and 4 mm wide. Apex apiculate. Upper surface colored near Green 137A, lower surface colored near Green 137B.

*Texture*.—Glabrous.

FLOWER

Natural flowering season: Spring until Autumn.
Inflorescence type and habit: Singly occurring fully double rotate flowers.
Rate of flower opening: Approximately 4 days from bud to fully opened flower.
Flower longevity on plant: 10 to 14 days, after fully opened.
Quantity of flowers: 20 to 30 fully opened flowers and buds.
Flower size:
*Diameter*.—Approximately 7.0 To 10.0 cm.
*Height*.—Approximately 5.0 cm.
Flower shape: Viewed from above, round.
Peduncle:
*Length*.—4.0 cm.
*Diameter*.—3 mm.
*Color*.—Near Green 143C.
*Texture*.—Prickly.
Petals:
*Petal arrangement*.—Multiple rotate, overlapping whorls.
*Petal quantity*.—45 to 60.
*Length*.—4.0 cm.
*Width*.—4.4 cm.
*Shape*.—Broad deltate.
*Margin*.—Entire.
*Apex*.—Rounded, narrow, slight ruffling at apex.
*Base*.—Very broad attenuate.
*Texture*.—Glabrous all surfaces.
Color: Petals.
*When opening*.—Upper surface: Near RHS Yellow 10B, center 10A, margin lightly flushed Red-Purple 61B. Lower surface: Near RHS Yellow 10B, center 10A.
*Fully opened*.—Upper surface: Near RHS Yellow 12D, medium basal center 12B. Uppermost margin Red-Purple N57A, descending to 61C, then a flush of 63C. Lower surface: Base near Yellow 12D, center 12A. Red-Purple 63B and 63C, mixed. Margin 67A and N57A.
*Color changes when aging*.—Upper surface: Near White 155C and Red-Purple 65D, margins heavily flushed Red-Purple 61B. Small basal blotch near Yellow 9A. Lower surface: Near White 155C and Red-Purple 69C, margins flushed Red-Purple 67A mixed with 61B. Small basal blotch near Yellow 9A.
Bud:
*Shape*.—Ovate.
*Length*.—Approximately 3 cm.
*Diameter*.—Approximately 2 cm.
*Color*.—Near Yellow 9C. Margin heavily flushed Red 45B. Stippling of Red 44B on edge of margin.
Sepals:
*Quantity*.—5.
*Length*.—3.2 cm, including elongated apiculate apex.
*Width*.—11 mm.
*Shape*.—Deltoid.
*Apex*.—Apiculate.
*Margin*.—Entire.
*Sepal extension*.—Moderate.
*Texture*.—Pubescent upper surface, glabrous lower surface.
*Color*.—Interior Surface: Near Green 138A. Basal flush near Red-Purple 59C. Exterior Surface: Near Green 138B.
Receptacle:
*Length*.—0.7 cm.
*Width*.—1.5 cm.
*Shape*.—Flattened dome.
*Color*.—Near Yellow-Green N144B.
Fragrance: Moderate typical tea rose scent.

REPRODUCTIVE ORGANS

Stamens:
*Quantity*.—About 100.
*Filament length*.—Approximately 4 to 11 mm.
*Filament color*.—Near Greyed-Orange 165D.
Anthers:
*Length*.—2 mm.
*Shape*.—Narrow globular.
*Color*.—Near Greyed-Orange 168A.
*Pollen*.—Color: Near Greyed-Orange 167A. Quantity: Scant or none.
Pistil: Not observed.

OTHER CHARACTERISTICS

Seeds and fruits: Not observed.
Disease/pest resistance: Good overall disease resistance to normal pests and diseases typical of garden roses. Very good resistance to blackspot diseases and powdery mildew.
Hardiness: Observed cold hardy to USDA Zone 6.

What is claimed is:

1. A new and distinct floribunda rose plant named 'ALT-sister' as herein illustrated and described.

* * * * *